(12) United States Patent
Flat et al.

(10) Patent No.: US 8,669,532 B2
(45) Date of Patent: *Mar. 11, 2014

(54) EVALUATING A CLEANING SOLUTION USING UV ABSORBANCE

(75) Inventors: Ariel Flat, Palo Alto, CA (US); Suraj Puri, Los Altos, CA (US)

(73) Assignee: Nano Green Technology, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,330

(22) Filed: Feb. 10, 2012

(65) Prior Publication Data

US 2012/0138813 A1 Jun. 7, 2012

Related U.S. Application Data

(63) Continuation of application No. 12/126,740, filed on May 23, 2008, now Pat. No. 8,138,482.

(51) Int. Cl.
*G01J 3/42* (2006.01)
*G01J 3/00* (2006.01)

(52) U.S. Cl.
USPC .......... 250/372; 250/336.1; 356/51; 356/433; 356/432

(58) Field of Classification Search
USPC .................. 250/372, 336.1; 356/51, 433, 432
See application file for complete search history.

(56) References Cited

U.S. PATENT DOCUMENTS

| | | |
|---|---|---|
| 6,799,583 B2 | 10/2004 | Puri et al. |
| 2006/0019849 A1 | 1/2006 | Puri |
| 2008/0047579 A1 | 2/2008 | Ji et al. |

*Primary Examiner* — Christine T Mui
(74) *Attorney, Agent, or Firm* — EcoTech Law Group, P.C.

(57) ABSTRACT

A process for evaluating a cleaning solution is described. The process includes: (a) subjecting a solution, including a solute and a solvent, to sonic energy to create a sonicated solution; (b) measuring UV absorption of the sonicated solution to produce a sample UV absorbance spectra; (c) obtaining a reference UV absorbance spectra; (d) scaling the reference UV absorbance spectra to the sample UV absorbance spectra at a lower range of the UV spectrum; (e) subtracting from the reference UV absorbance spectra the sample UV absorbance spectra to produce a differential UV spectra; and (f) evaluating at or near a peak of the sample UV absorbance spectra the differential UV absorbance spectra to determine whether the sonicated solution is activated.

15 Claims, 6 Drawing Sheets

EVALUATING A CLEANING SOLUTION USING UV ABSORBANCE

BACKGROUND OF THE INVENTION

This application is a continuation of prior application Ser. No. 12/126,740, filed May 23, 2008, entitled "EVALUATING A CLEANING SOLUTION USING UV ABSORBANCE", by inventors Puri et al., from which priority under 35 U.S.C. §120 is claimed which is incorporated herein by reference in its entirety for all purposes The present invention relates generally to cleaning solutions used in a wide variety of cleaning applications. More particularly, the present invention relates to evaluating the effectiveness of a sonicated cleaning solution used for cleaning substrates.

U.S. patent application Ser. No. 10/886,785, filed on Jul. 7, 2004, entitled "Systems and Methods for Charging a Cleaning Solution User for Cleaning Integrated Circuit Substrates" and U.S. patent application Ser. No. 11/093,904, filed on Mar. 29, 2005, entitled "Systems and Methods for Single Integrated Substrate Cleaning and Rinsing," among other things, disclose cleaning IC substrates using a sonicated solution. The sonicated solution is produced by applying acoustic energy (e.g., megasonic energy) to a solution containing a solute. In a subsequent step, the sonicated solution is used to effectively clean the IC substrate.

The above-mentioned sonicated solution offers advantages that are not realized by the conventional cleaning solutions, which employ a concentrated ammonia hydroxide solution known as the Standard Cleaning Solution 1 (the "SC-1 solution"). In fact, cleaning using concentrated solutions suffers from several drawbacks that are not encountered when cleaning using sonicated solutions, which are extremely effective, under superdilute or near zero dilutions. Concentrated solutions run the risk of unduly etching, which appears as surface roughness and causes damage to the substrate surface and devices undergoing cleaning. In a non-patterned IC substrate, for example, over etching damages the real estate on the substrate surface, upon which circuitry and transistor devices are subsequently fabricated. For this reason, the resulting semiconductor chip may suffer from poor electrical performance or complete malfunction.

Dispensing highly concentrated cleaning solutions to drain poses environmental concerns. As a result, the concentrated effluent stream exiting the clean system requires appropriate treatment. The cost of an effluent treatment system and labor to implement the cleanup process make cleaning using the SC-1 solution expensive.

Concentrated cleaning solution also deposit on the surface undesirable metal contaminants which degrade device performance. Moreover, the peroxide composition of the cleaning solution typically contains stabilizers, which is another source of contamination that leads to performance issues. The problem is further exacerbated when relatively high composition of peroxide is used as part of the cleaning solution.

Of particular concern is cleaning integrated circuit ("IC") substrates, including semiconductor substrates, that require removal of contaminant particles which adversely impact current circuit geometries. With the miniaturization of the circuitry on ICs, device sizes are currently approaching progressively smaller scales and such small devices densely populate the IC substrate surface. Contaminant particles of a certain size, which previously did not pose a threat to an IC's performance because the early generation of ICs were not as densely populated, now have a significant impact on the electrical performance of current ICs having miniature geometries. In fact, the contaminant particles can render the IC useless. As a result, an effective cleaning method for removing such contaminant particles, without damaging the substrate surface, is critical to enhancing the yield of ICs.

As a result, IC fabrication facilities are selecting the above-mentioned sonicated cleaning solution to replace the SC-1 cleaning solution, which has been the cleaning solution of choice for most in the semiconductor industry during the last forty years.

Unfortunately, currently there exists no objective method for evaluating the effectiveness of a sonicated cleaning solution in a cleaning process.

What is, therefore, needed is a method for evaluating the effectiveness of a sonicated cleaning solution in a cleaning process.

SUMMARY OF THE INVENTION

In view of the foregoing, this invention provides a process for evaluating a cleaning solution. The process includes: (i) subjecting a solution, including a solute and a solvent, to sonic energy to create a sonicated solution; (ii) measuring UV absorption of the sonicated solution to produce a sample UV absorbance spectra; (iii) obtaining a reference solution, which includes a solute concentration that is similar to that of solute concentration in the sonicated solution; (iv) measuring UV absorption of the reference solution to produce a reference UV absorbance spectra; (v) scaling the reference UV absorbance spectra to the sample UV absorbance spectra at a lower range of the UV spectrum; (vi) subtracting from the reference UV absorbance spectra the sample UV absorbance spectra to produce a differential UV spectra; and (vii) evaluating at or near a peak of the sample UV absorbance spectra the differential UV absorbance spectra to determine whether the sonicated solution is activated.

If it is determined from evaluating that the sonicated solution is not activated, then in accordance with one embodiment of the present invention, the following steps are performed: (i) further subjecting the solution to sonic energy to create a more sonicated solution; (ii) measuring UV absorption of the more sonicated solution to produce a second sample UV absorbance spectra; (iii) scaling the reference UV absorbance spectra to the second sample UV absorbance spectra at a lower range of the UV spectrum; (iv) subtracting from the reference UV absorbance spectra the second sample UV absorbance spectra to produce a differential UV spectra; and (v) evaluating at or near a peak of the second sample UV absorbance spectra the differential UV absorbance spectra to determine whether the more sonicated solution is activated.

In one embodiment of the present invention, the solute is present in the solvent in a volumetric ratio that is between about $5 \times 10^{-5}:1$ and about $1 \times 10^{-24}:1$. Preferably, the solute is present in the solvent in a volumetric ratio that is between about $1 \times 10^{-6}:1$ and about $1 \times 10^{-24}:1$. More preferably, the solute is present in the solvent in a volumetric ratio that is between about $1 \times 10^{-8}:1$ and about $1 \times 10^{-24}:1$.

The solute may be one member selected from a group consisting of $NH_4$, $O_3$, $HCl$, $H_2O_2$, $NH_4OH$ and $HF$. The solvent is preferably deionized water. The megasonic energy may be 400 Watts or higher. The step of measuring UV absorption of the sonicated solution includes using a UV spectrophotometer. The lower range of the UV spectrum is a range between about 190 nm and 220 nm. The step of evaluating includes determining whether the sample UV absorbance spectra is larger than the corresponding signal of the reference solution. The step of subjecting the sonicated solution includes subjecting the sonicated solution to megasonic energy for a duration that is between about 10 minutes and about 2 hours. This duration typically depends on the amount of megasonic energy that is supplied to the solution.

In another aspect, the present invention provides a process of determining degree of activation of a solution. The process includes: (i) obtaining a standard peak height from a differential UV absorbance spectra of a solution that is sufficiently activated to accomplish at least 99% particle removal efficiency; (ii) determining a sample peak height from a differential UV absorbance spectra of a sample solution; and comparing said sample peak height to said standard peak height to determine a degree of activation for said sample solution.

The method of operation of the invention, however, together with additional objects and advantages thereof will be best understood from the following descriptions of specific embodiments when read in connection with the accompanying figures.

DETAILED DESCRIPTION OF THE PREFERRED EMBODIMENTS

In the following description numerous specific details are set forth in order to provide a thorough understanding of the present invention. It will be apparent, however, to one skilled in the art that the present invention may be practiced without limitation to some or all of these specific details. In other instances, well known process steps have not been described in detail in order to not unnecessarily obscure the invention.

Figure 1:
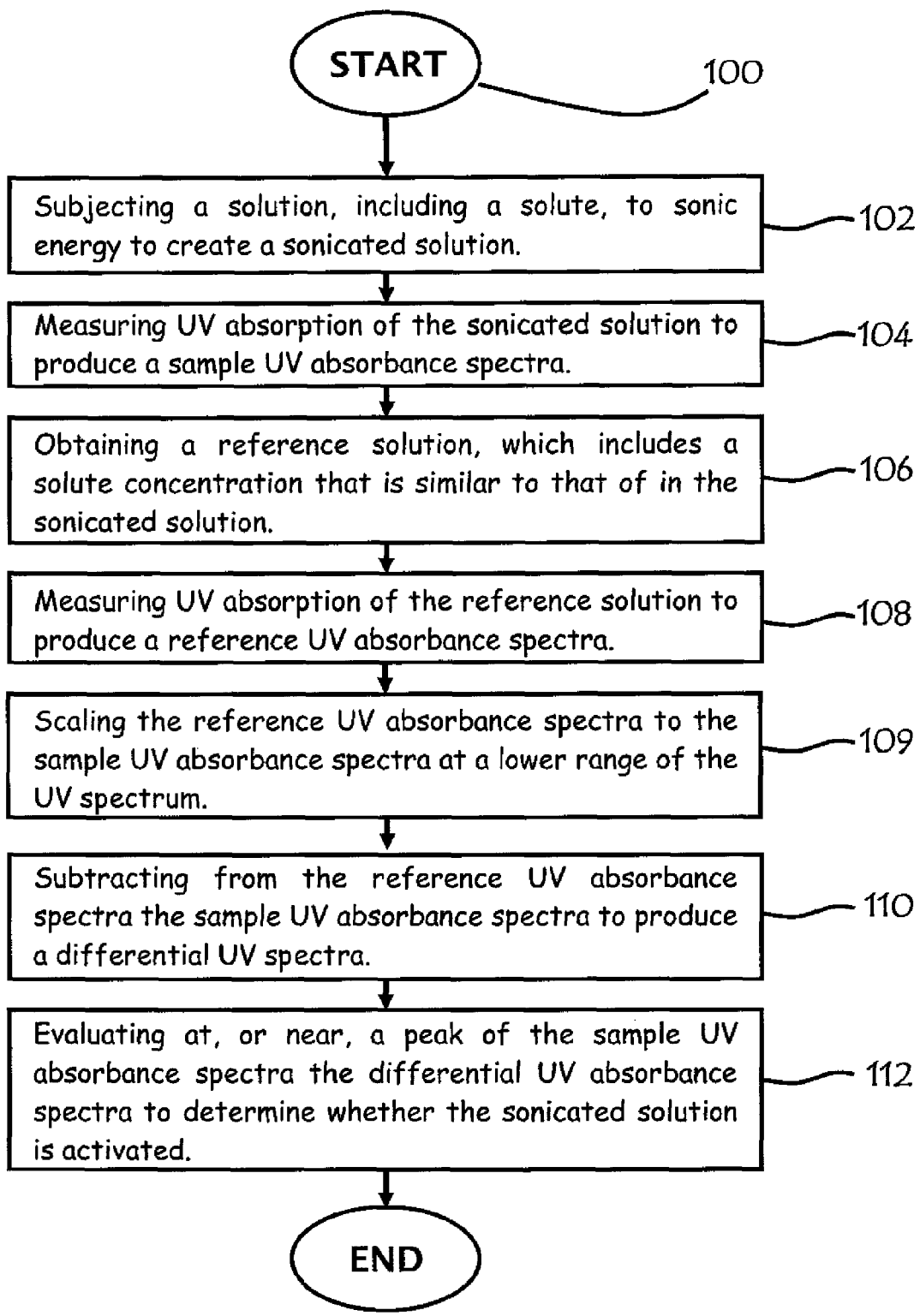
FIG. 1 shows a process flow diagram of a process, according to one embodiment of the present invention, for evaluating a sonicated cleaning solution.

FIG. 1 shows a process flow diagram of a process 100, according to one embodiment of the present invention, for evaluating a sonicated cleaning solution. In this embodiment of the present invention and in step 102, the solution designed for cleaning, which includes one solute and a solvent, is subjected to sonic energy to produce a sonicated solution. The sonic energy provided may be ultrasonic energy, but is preferably megasonic energy. The sonic energy supplied to the solution may be for a duration that is between about 10 minutes and about 2 hours. This duration depends on the amount of sonic energy supplied to the solution.

In step 104, UV absorption of the sonicated solution is measured to produce a sample UV absorbance spectra. Preferably, a CARY 50 spectrophotometer, which is commercially available from Varian, Inc. of Palo Alto, Calif., is used to make such UV absorption measurements. By way of example, FIG. 2, which is a plot of absorbance versus wavelength, shows a UV absorbance spectra 202 for a sample and is labeled "Sample."

Figure 2:
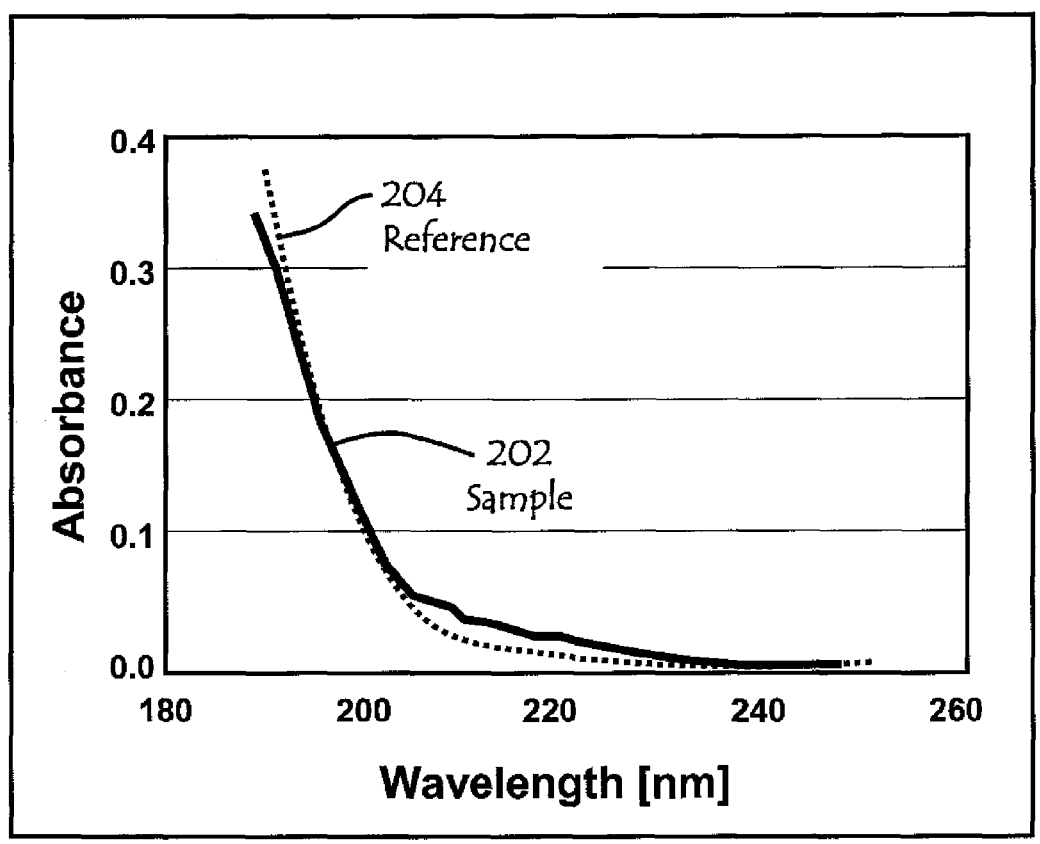
FIG. 2 shows a plot of absorbance versus wavelength for a sonicated solution and a non-sonicated solution.

The next two steps 106 and 108 are carried out to obtain a reference UV absorption spectra, which provides the baseline curve against which a sonicated solution can be analyzed. In step 106, a reference solution, which includes a solute concentration that is similar to the solute concentration in the sonicated solution, is obtained. For a reference solution to be deemed similar, the solute concentration in the reference solution should be proximate enough to the solute concentration in the sonicated solution, such that an absorbance measurement of the reference solution effectively quantifies the contribution of the solute in the sonicated solution to the absorbance of the sonicated solution. By way of example, the solute concentration in the reference solution should be within between about 5% and about 10% of the solute concentration in the sonicated solution. In step 108, the UV absorption of the reference solution is measured much in the same way the UV absorption of the sonicated solution is measured in step 104. This UV absorption measurement of the reference solution produces a reference UV absorbance spectra. By way of example, FIG. 2 shows a UV absorbance spectra 204 for a reference solution and is labeled "Reference."

Step 109 calls for scaling the reference UV absorbance spectra to the sample UV absorbance spectra at a lower range of the UV spectrum. There is no rigid number for the lower range of the UV spectrum. Those skilled in the art will, however, appreciate that lower wavelengths at which absorbance measurements will be the wavelengths at which scaling is initiated. Furthermore, those skilled in the art may also think of this step as calibrating or normalizing the absorbance measurement of the sonicated solution with a reference solution.

Figure 4:
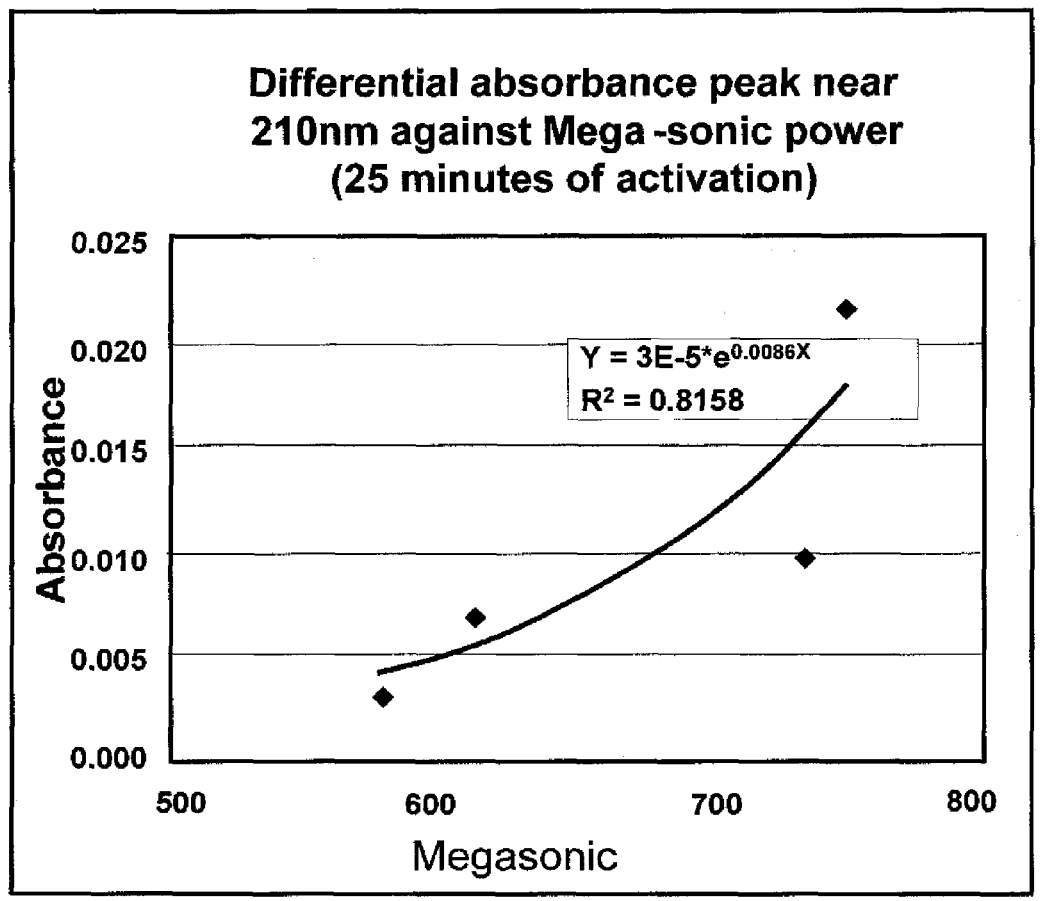
FIG. 4 shows a plot, at or near 210 nm, of differential absorbance peak versus the amount of megasonic energy supplied to the sonicated solution.

In a next step 110, from the reference UV absorbance spectra the sample UV absorbance spectra is subtracted to produce a differential UV absorbance spectra. FIG. 4, which is plot of differential signal versus wavelength, shows a differential UV absorbance spectra. In this step, the contribution of the solute to the absorbance measurement of the sonicated solution is accounted for, and thereby leaving behind to quantify the contribution of the activated state, if present, of the sonicated solution to the absorbance measurement of the sonicated solution.

Figure 3:
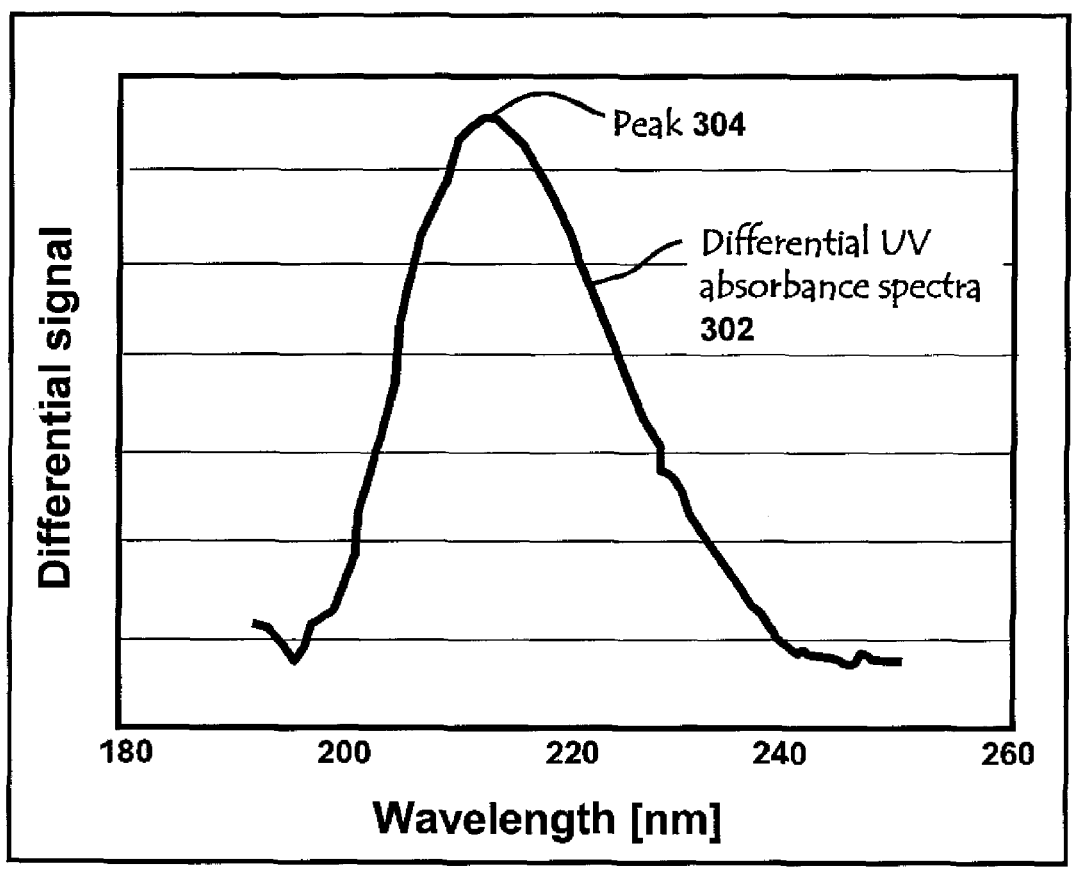
FIG. 3 shows a plot of differential UV spectra between the sonicated and the non-sonicated solutions versus wavelength.

In Step 112, at or near a peak of the sample UV absorbance spectra, the differential UV absorbance spectra is evaluated. FIG. 3 shows such a distinct peak 304. The differential UV absorbance spectra quantifies the contribution of the activated state of the sonicated solution to the absorbance measurement of the sonicated solution and at the peak such contribution of the activated state appears to be recorded in a pronounced manner and, therefore, more susceptible to measurement.

FIG. 4 shows a plot of absorbance versus megasonic energy near a wavelength of 210 nm for a sonicated solution that was subjected to megasonic energy for 25 minutes. The megasonic instrument used for supplying the requisite sonic energy to obtained measurements shown in FIGS. 4, 5 and 6 had a power density of 1.5 Watts/cm$^2$. According to this plot, the absorbance of a sonicated solution almost linearly rises with increased megasonic energy. In other words, it appears that when the megasonic energy supplied to a solution is increased, the UV absorbance measurement of that solution is almost proportionately increased. This indicates that the sonicated solution achieves a progressively higher or greater activated state when treated with increasing megasonic energies for 25 minutes.

While not wishing to be bound by theory, it is believed that in activated state of a solution, the solute is coherent—where the solute and solvent molecules are organized, as opposed to being randomly distributed in the solution's non-activated state. In an activated state of a solution, one or more solute molecules are surrounded by many solvent molecules to form solute clusters. Furthermore, supplying high amounts of megasonic energy for longer periods of time, up to a certain limit, typically intensifies formation of such solute clusters. Previously mentioned U.S. patent application Ser. Nos. 10/886,785 and 11/093,904, which are incorporated herein by reference in their entirety for all purposes, disclose that such solute clusters effectively clean a substrate surface by removing contaminant particles. By way of example, FIG. 2A of U.S. patent application Ser. No. 10/886,785 shows randomly distributed solute particles in a non-activated solution and FIG. 2B of the same application shows organized solute clusters in an activated solution. An activated solution may be called a "charged solution," because this organized state of the solute and solvent imparts a charge to the solution and a non-zero electromotive force (EMF) for the solution can be measured.

Referring back to step 112 of FIG. 1, in the event it is determined from the evaluating step that the sonicated solution is not activated, then the sonicated solution is further subjected to sonic energy to create a more sonicated solution, the UV absorption of which is measured, similar to that described in step 104 of FIG. 1, to produce a second sample UV absorbance spectra. Reference UV absorbance spectra, which was previously established, is then employed at a lower range of the UV spectrum, as in step 109 of FIG. 1, to scale it relative to the second sample UV absorbance spectra. Next, from the reference UV absorbance spectra the second sample UV absorbance spectra is subtracted to produce a differential UV spectra and at or near a peak of the second sample UV absorbance spectra. This differential spectra is analyzed to determine whether the more sonicated solution is activated. In this manner, a feedback loop is created to supply more sonic energy to a sonicated solution until that sonicated solution is activated.

An analysis to determine whether a sonicated solution is activated may be expedited by forming a library of reference solutions in advance. In this library, solutions with various solute concentrations, treated with different amounts of megasonic energies and for different durations of time would be correlated with their absorbance measurements. Such a library obviates the need to create a reference UV absorbance spectra during the analysis of a sonicated solution and increases the throughput of the cleaning process. A cleaning process follows a determination that the sonicated solution is indeed activated and, therefore, ready for cleaning.

Figure 5:
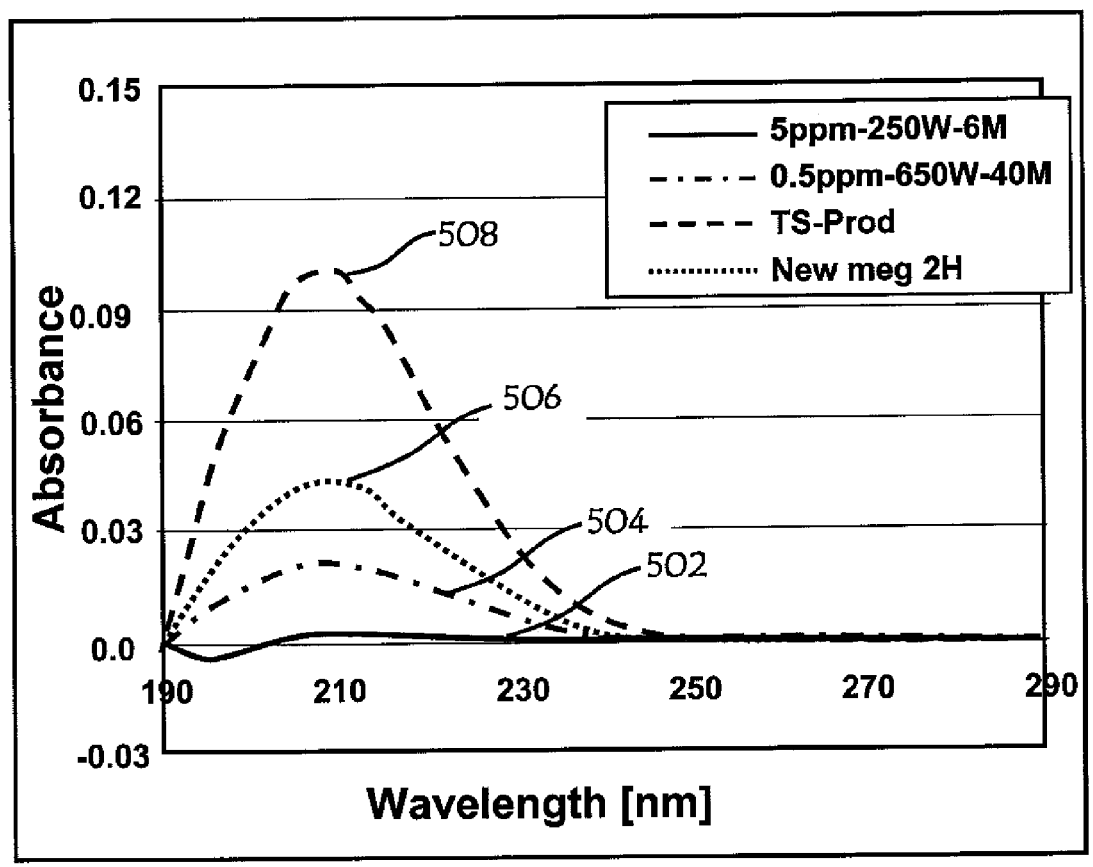
FIG. 5 shows a plot of differential UV spectra versus wavelength for different cleaning solutions.

FIG. 5 shows a plot of absorbance versus wavelength for various solutions as examples. A first curve 502 labeled "5 ppm-250W-6M," describes the absorbance measurement of a 5 ppm ammonium hydroxide solution which was subject to megasonic energy at a setting of 250 W for 6 minutes. According to this curve, at or near 210 nm wavelength, a low UV absorbance measurement indicates little or no activation.

A second curve 504 labeled "5 ppm-650W-40M," describes the absorbance measurement also of a 5 ppm ammonium hydroxide solution which was subject to a greater megasonic energy of about 650 Watts for a duration of about 40 minutes. An increased duration of megasonic energy shows a relatively larger absorbance peak at or near 210 nm. In other words, it is believed that increased duration of megasonic treatment translates into a higher degree of activation.

A third curve 508 labeled "TS-Prod" describes the absorbance measurement of a 0.8 ppm ammonium hydroxide solution that was subjected to a megasonic energy that is between about 680 Watts and about 690 Watts for a duration that is approximately between about 1.5 and about 2 hours, including intermittent interruptions in the supply of megasonic energy. It is important to note that the 0.8 ppm ammonium hydroxide solution was prepared during a preactivation process that lasted for about 45 minutes.

The preactivation process, which according to a preferred embodiment of the present invention, includes obtaining or preparing a 10 ppm solution of ammoniated water, then serially diluting that concentrated solution using a recirculating scheme, which gradually introduces deionized water for achieving intermediate levels of dilution. During the preactivation, the various intermediate dilutions are subjected to a megasonic energy that is between about 680 and about 690 Watts.

Referring back to curve 508 in FIG. 5, at or near 210 nm, the curve appears to indicate that increased megasonic energy for longer durations translates into a higher degree of activation. In the example of curve 508, it is believed that additional megasonic energy during the preactivation stage enhanced the extent of activation.

A fourth curve 506 labeled "New meg 2H" describes the absorbance measurement of a 1 ppm ammonium hydroxide solution which was subject to megasonic energy at a setting of 670 W for 2 hours. At or near 210 nm, curve 506 shows a relatively high peak, but not as large as that of curve 508. While wishing not to be bound by theory, it is believed that preactivation, which includes supplying megasonic energy above and beyond the activating process, enhances the degree of activation of the solution because it provides mixing for prolonged periods of time.

Figure 6:
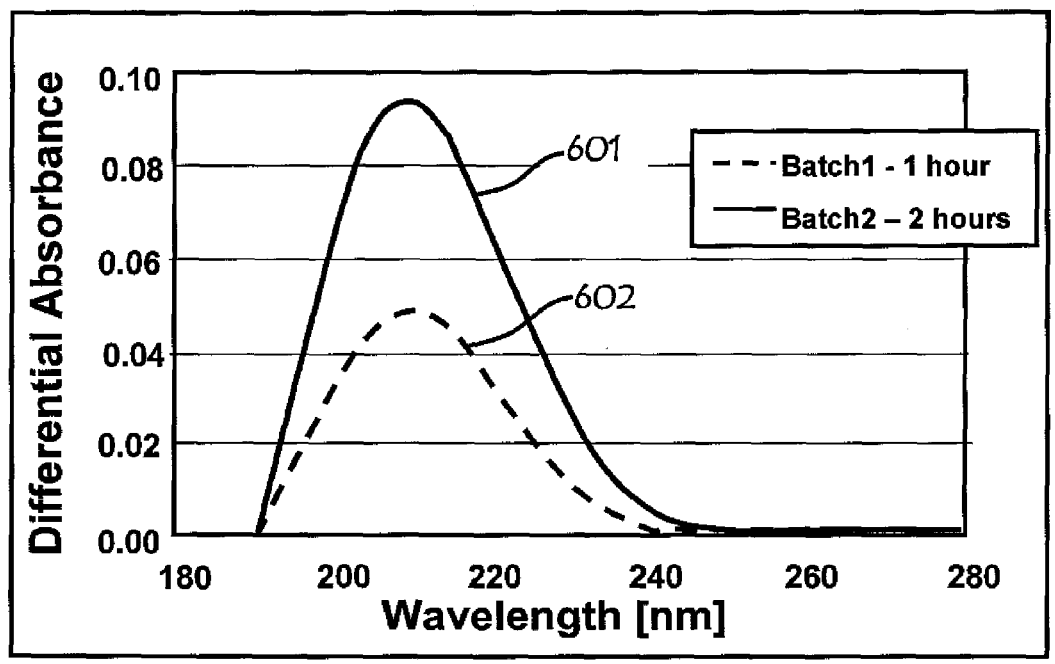
FIG. 6 shows a plot of differential absorbance versus wavelength for two different solutions, each with a different duration of sonic energy treatment than the other.

FIG. 6 shows a plot of differential absorbance versus wavelength for two separate solutions, each of which is an about 0.8 ppm ammonium hydroxide solution activated using megasonic energy of about 675 Watts. The solution underlying the differential absorbance spectra represented by curve 601, and has a similar concentration of ammonium hydroxide as the solution underlying the absorbance spectra represented by curve 508 of FIG. 5. The solution underlying curve 601 was subjected to the above-mentioned megasonic energy for about 2 hours. The solution underlying the curve 602 was similarly subjected to megasonic energy for about 1 hour.

Cleaning substrates using the solution underlying curve 601 provides a 99% particle removal efficiency (PRE), which is a well known metric to quantify a cleaning process in the substrate cleaning industry. It appears that a cleaning solution with a higher differential absorbance (e.g., curve 601 of FIG. 1) more effectively cleans the substrate surface than a cleaning solution with a relatively lower differential absorbance (e.g., curve 602 of FIG. 1). In other words, a solution with a higher degree of activation will clean more effectively. If the solution underlying curve 601 is deemed fully activated (i.e., has achieved 100% activation), then the corresponding absorbance spectra's peak height (e.g., at or near 210 nm) serves as a standard, against which peak heights of other activated solutions can be measured to determine their degree of activation relative to the fully activated solution. Using curves 601 and 602 of FIG. 6 as examples, and given that at or near 210 nm, the peak height of curve 602 is a little more than half as large as the peak height of curve 601, it is believed that the solution underlying curve 601 is a little more than half the way from being fully activated.

In light of the above, the present invention provides a method for determining the extent of activation for a solution. In one embodiment of the present invention, this method begins by obtaining a solution with maximum activation (i.e., sufficient activation to accomplish at least 99% PRE). For example, this degree of activation can be obtained by subjecting a solution, including a solute and a solvent, to large amounts of megasonic energies for long durations, as described above with reference to FIGS. 4, 5 and 6. The next steps call for obtaining a differential absorbance spectra, as described in FIG. 1, and then establishing the peak height of the differential absorbance spectra as a standard peak height.

In this embodiment, the process now includes analyzing the differential absorbance spectra of a sample that has undergone sonic treatment as described in FIG. 1. The resulting peak height from the differential absorbance spectra of the sample is then compared against the standard peak height determined in previous step to arrive at a percentage of activation. In this manner, sufficiently activated cleaning solutions can be produced to effectively clean a wide variety of substrates, which are not limited to, but include integrated circuit substrates.

Although illustrative embodiments of this invention have been shown and described, other modifications, changes, and substitutions are intended. Accordingly, it is appropriate that the appended claims be construed broadly and in a manner consistent with the scope of the disclosure, as set forth in the following claims.

What is claimed is:

1. A process for evaluating a cleaning solution, comprising:
   subjecting a solution, including a solute and a solvent, to sonic energy to create a sonicated solution;
   measuring UV absorption of said sonicated solution to produce a sample UV absorbance spectra;
   obtaining a reference UV absorbance spectra;
   scaling said reference UV absorbance spectra to said sample UV absorbance spectra at a lower range of said UV spectrum;
   subtracting from said reference UV absorbance spectra said sample UV absorbance spectra to produce a differential UV spectra; and
   evaluating at or near a peak of said sample UV absorbance spectra said differential UV absorbance spectra to determine whether said sonicated solution is activated.

2. The process of claim 1, wherein if it is determined from said evaluating that said sonicated solution is not activated, then:
   further subjecting said solution to sonic energy to create a more sonicated solution;
   measuring UV absorption of said more sonicated solution to produce a second sample UV absorbance spectra;
   scaling said reference UV absorbance spectra to said second sample UV absorbance spectra at a lower range of said UV spectrum;
   subtracting from said reference UV absorbance spectra said second sample UV absorbance spectra to produce a differential UV spectra; and
   evaluating at or near a peak of said second sample UV absorbance spectra said differential UV absorbance spectra to determine whether said more sonicated solution is activated.

3. The process of claim 1, wherein said solute present in said solvent in a volumetric ratio that is between about $5\times10^{-5}:1$ and about $1\times10^{-24}:1$.

4. The process of claim 3, wherein said solute present in said solvent in a volumetric ratio that is between about $1\times10^{-6}:1$ and about $1\times10^{-24}:1$.

5. The process of claim 4, wherein said solute present in said solvent in a volumetric ratio that is between about $1\times10^{-8}:1$ and about $1\times10^{-24}:1$.

6. The process of claim 1, wherein said solute is one member selected from a group consisting of $NH_4$, $O_3$, $HCl$, $H_2O_2$, $NH_4OH$ and $HF$.

7. The process of claim 1, wherein said subjecting includes subjecting said solution to ultrasonic or megasonic energy.

8. The process of claim 1, wherein said subjecting includes subjecting said solution to megasonic energy of 400 Watts or higher.

9. The process of claim 1, wherein said measuring UV absorption of said sonicated solution includes using a UV spectrophotometer.

10. The process of claim 1, wherein said lower range of said UV spectrum is a range between about 190 nm and 225 nm.

11. The process of claim 1, wherein said evaluating includes determining whether the sample UV absorbance spectra is larger than the corresponding reference UV absorbance spectra.

12. The process of claim 1, wherein said subjecting said sonicated solution includes subjecting said sonicated solution to megasonic energy for a duration that is between about 10 minutes and about 2 hours.

13. The process of claim 1, wherein said solvent is deionized water.

14. The process of claim 1, wherein said obtaining includes obtaining said reference UV absorbance spectra from a library.

15. The process of claim 14, wherein said library correlates absorbance measurement of said solution with different solute concentrations in said solution, different amounts of with acoustic energies applied to said solution and durations of acoustic treatment.

* * * * *